US009709786B2

(12) United States Patent
Fukutake

(10) Patent No.: US 9,709,786 B2
(45) Date of Patent: Jul. 18, 2017

(54) NON-LINEAR MICROSCOPY AND NON-LINEAR OBSERVATION METHOD

(71) Applicant: Nikon Corporation, Chiyoda-ku, Tokyo (JP)

(72) Inventor: Naoki Fukutake, Tokyo (JP)

(73) Assignee: NIKON CORPORATION, Tokyo (JP)

( * ) Notice: Subject to any disclaimer, the term of this patent is extended or adjusted under 35 U.S.C. 154(b) by 134 days.

(21) Appl. No.: 14/020,806

(22) Filed: Sep. 7, 2013

(65) Prior Publication Data

US 2014/0009826 A1      Jan. 9, 2014

Related U.S. Application Data

(63) Continuation of application No. PCT/JP2012/001558, filed on Mar. 7, 2012.

(30) Foreign Application Priority Data

Mar. 7, 2011    (JP) .................... 2011-049415

(51) Int. Cl.
*G02B 21/06* (2006.01)
*G02B 21/16* (2006.01)
(Continued)

(52) U.S. Cl.
CPC .............. *G02B 21/06* (2013.01); *G01N 21/65* (2013.01); *G02B 21/002* (2013.01); *G02B 21/16* (2013.01);
(Continued)

(58) Field of Classification Search
CPC ........ G02B 21/24; G02B 21/14; G02B 21/22; G02B 21/06; G02B 21/00; G02B 21/082;
(Continued)

(56) References Cited

U.S. PATENT DOCUMENTS

| 5,386,112 A | 1/1995 | Dixon |
| 6,051,835 A * | 4/2000 | Pettipiece ............ G01J 3/2823 |
| | | 250/339.09 |

(Continued)

FOREIGN PATENT DOCUMENTS

| EP | 0 536 273 A1 | 4/1993 |
| EP | 1 223 451 A2 | 7/2002 |

(Continued)

OTHER PUBLICATIONS

International Search Report from International Patent Application No. PCT/JP2012/001558, May 29, 2012.

(Continued)

*Primary Examiner* — Jie Lei
(74) *Attorney, Agent, or Firm* — Shapiro, Gabor and Rosenberger, PLLC

(57) ABSTRACT

A non-linear microscopy includes an illuminating unit collecting an illuminating light supplied from a light source on a specimen and making a coherent non-linear optical process takes place at a collecting point; a detecting unit detecting a coherent object light occurred in the non-linear optical process and generating a signal indicating light intensity at a light detecting part; and a controlling unit scanning a specimen plane of the specimen by the collecting point and measuring a distribution of the signal on the specimen plane; in which at least one of an optical path of the illuminating light from the light source toward the specimen and an optical path of the object light from the specimen toward the light detecting part is duplicated to a pair of optical paths, and a relationship between the pair of optical paths is set to a symmetric relationship with respect to the specimen plane.

14 Claims, 5 Drawing Sheets

(51) Int. Cl.
*G02B 21/18* (2006.01)
*G02B 27/58* (2006.01)
*G02B 21/00* (2006.01)
*G01N 21/65* (2006.01)

(52) U.S. Cl.
CPC ............ *G02B 21/18* (2013.01); *G02B 27/58* (2013.01); *G01N 2021/653* (2013.01)

(58) Field of Classification Search
CPC ........ G02B 21/26; G02B 21/18; G02B 21/16; G02B 21/002; G02B 27/58; B82Y 15/00; B82Y 20/00; G01N 21/65; G01N 2021/659; G01B 9/02
USPC ............... 359/368, 371, 372, 385, 389, 392; 250/201.3, 216, 234; 356/301, 489
See application file for complete search history.

(56) References Cited

U.S. PATENT DOCUMENTS

| | | | |
|---|---|---|---|
| 7,333,207 | B2 | 2/2008 | Bewersdorf et al. |
| 2001/0030803 | A1 | 10/2001 | Engelhardt et al. |
| 2002/0105722 | A1 | 8/2002 | Bewersdorf et al. |
| 2005/0006597 | A1 | 1/2005 | Wolleschensky et al. |
| 2006/0291043 | A1* | 12/2006 | Bewersdorf et al. ......... 359/371 |
| 2007/0121119 | A1 | 5/2007 | Martinez |
| 2008/0259345 | A1 | 10/2008 | Fukutake |

FOREIGN PATENT DOCUMENTS

| | | |
|---|---|---|
| JP | 05-508031 A | 11/1993 |
| JP | 2001-356274 A | 12/2001 |
| JP | 2002-107301 A | 4/2002 |
| JP | 2002-221668 A | 8/2002 |
| JP | 2005-037388 A | 2/2005 |
| JP | 2009-047435 A | 3/2009 |
| JP | 2009-222531 A | 10/2009 |
| JP | 2012-073152 A | 4/2012 |
| WO | WO 2008/123408 A1 | 10/2008 |

OTHER PUBLICATIONS

Extended European Search Report issued Aug. 19, 2014, in European Patent Application No. 12 75 5122.

English translation of International Preliminary Report on Patentability from International Patent Application No. PCT/JP2012/001558, Sep. 19, 2013.

Office Action issued Nov. 30, 2015, in Chinese Patent Application No. 201280012144.8.

Office Action issued Feb. 16, 2016, in Japanese Patent Application No. 2013-503394.

\* cited by examiner

RESONANT PROCESS
(CARS PROCESS)
(A)

NON-RESONANT
PROCESS
(B)

BILATERAL EXCITATION & BILATERAL DETECTION MODE

BILATERAL EXCITATION & UNILATERAL DETECTION MODE

UNILATERAL EXCITATION & BILATERAL DETECTION MODE

TRANSMITTING OBSERVATION MODE

REFLECTING OBSERVATION MODE

NON-LINEAR MICROSCOPY AND NON-LINEAR OBSERVATION METHOD

CROSS-REFERENCE TO THE RELATED APPLICATION

This application is a continuation application of International Application PCT/JP2012/001558, filed Mar. 7, 2012, designating the U.S., and claims the benefit of priority from Japanese Patent Application No. 2011-049415, filed on Mar. 7, 2011, the entire contents of which are incorporated herein by reference.

BACKGROUND

1. Field

The present application relates to a non-linear microscopy and a non-linear observation method.

2. Description of the Related Art

In recent years, a momentum of biotechnology industry is skyrocketing, and in particular, a demand for three-dimensional resolution microscopy in which a biological sample is set as an observational object, is increasing more and more. In the three-dimensional resolution microscopy, a confocal microscopy with high spatial resolution has been widely used from old times to present time. A conventional confocal microscopy observes a fluorescence generated, by a fluorescence molecule contained in a biological sample, in a linear intensity with respect to an intensity of irradiating light (a signal obtained through a linear optical process), and in recent years, a non-linear microscopy that observes a light generated, by a specific kind of molecule contained in a biological sample, in a non-linear intensity with respect to an intensity of irradiating light (a signal obtained through a non-linear optical process), has been drawing an attention.

The non-linear microscopy uses a light with relatively long wavelength (near-infrared ray, for example) as the irradiating light, so that the sample can be observed up to a deep portion thereof. Further, since the aforementioned non-linear process takes place only in a minute region in the vicinity of a focus of an objective lens, an image obtained by the non-linear microscopy becomes an image of an extremely thin layer (sectioning image). As one of such non-linear microscopy, there is a CARS microscopy that utilizes a coherent anti-Stokes Raman scattering (CARS) as the non-linear process (refer to Japanese Unexamined Patent Application Publication No. 2009-47435 and the like).

However, the conventional CARS microscopy has a problem that a resolution in an optical axis direction (z direction) is lower than a resolution in an inplane direction (xy direction) perpendicular to the optical axis.

Accordingly, the present application has a proposition to provide a non-linear microscopy and a non-linear observation method capable of increasing a resolution in an optical axis direction.

SUMMARY

One aspect of a non-linear microscopy of the present embodiment is a non-linear microscopy including an illuminating unit collecting an illuminating light supplied from a light source on a specimen and making a coherent non-linear optical process takes place at a collecting point at which the illuminating light is collected; a detecting unit detecting a coherent object light occurred in the non-linear optical process at the collecting point and generating a signal indicating light intensity at a light detecting part at which the object light is detected; and a controlling unit repeatedly acquiring the signal generated by the detecting unit while scanning a specimen plane of the specimen by the collecting point and measuring a distribution of the signal on the specimen plane; in which at least one of an optical path of the illuminating light directed from the light source toward the specimen and an optical path of the object light directed from the specimen toward the light detecting part is duplicated to a pair of optical paths, and a relationship between the pair of optical paths is set to a symmetric relationship with respect to the specimen plane.

Further, one aspect of a non-linear microscopy of the present embodiment includes a beam splitter splitting an optical path of an illuminating light supplied from a light source into a pair of optical paths, a pair of deflecting mirrors individually deflecting the pair of optical paths toward mutually opposite sides of a specimen plane of a specimen, a pair of objective lenses individually disposed on the pair of optical paths and focusing on a common position on the specimen plane, a dichroic mirror disposed on a common part of the pair of optical paths and separating a coherent object light occurred in a non-linear optical process at a collecting point of the pair of objective lenses from the illuminating light, a detecting unit detecting the object light separated by the dichroic mirror and generating a signal indicating light intensity at a light detecting part at which the object light is detected, and a controlling unit repeatedly acquiring the signal generated by the detecting unit while scanning the specimen plane by the collecting point and measuring a distribution of the signal on the specimen plane.

Further, one aspect of a non-linear observation method of the present embodiment is a non-linear observation method including an illuminating step collecting an illuminating light supplied from a light source on a specimen and making a coherent non-linear optical process takes place at a collecting point at which the illuminating light is collected; a detecting step detecting a coherent object light occurred in the non-linear optical process at the collecting point and generating a signal indicating light intensity at a light detecting part at which the object light is detected; and a controlling step repeatedly acquiring the signal generated in the detecting step while scanning a specimen plane of the specimen by the collecting point and measuring a distribution of the signal on the specimen plane; in which at least one of an optical path of the illuminating light directed from the light source toward the specimen and an optical path of the object light directed from the specimen toward the light detecting part are duplicated to a pair of optical paths, and a relationship between the pair of optical paths is set to a symmetric relationship with respect to the specimen plane.

According to the present application, a non-linear microscopy and a non-linear observation method capable of increasing a resolution in an optical axis direction are realized.

DETAILED DESCRIPTION OF THE EMBODIMENTS

First Embodiment

Hereinafter, a first embodiment of the present invention will be described. The present embodiment is an embodiment of a CARS microscopy.

Figure 1:
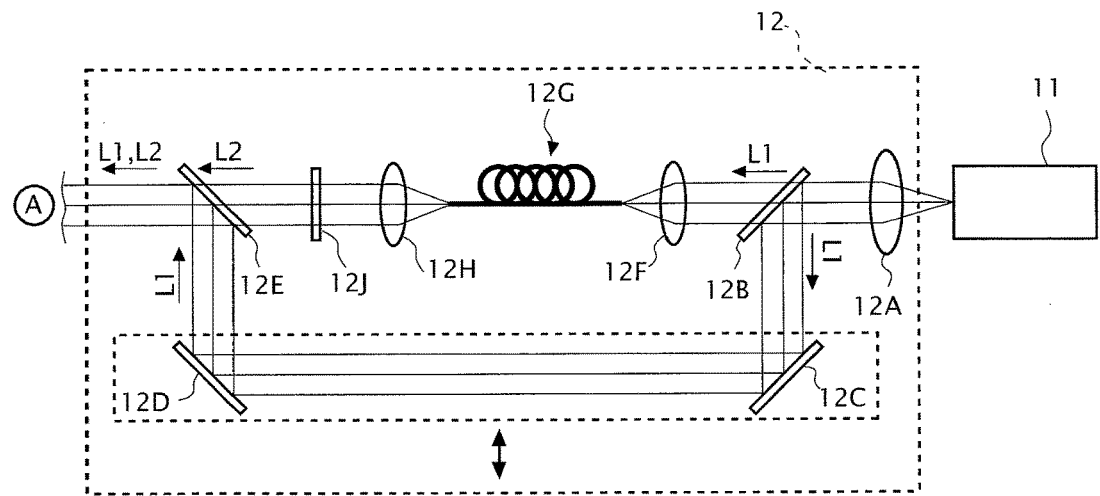
FIG. 1 is a configuration diagram of a CARS microscopy of the present embodiment (bilateral excitation & bilateral detection mode).
Figure 1:
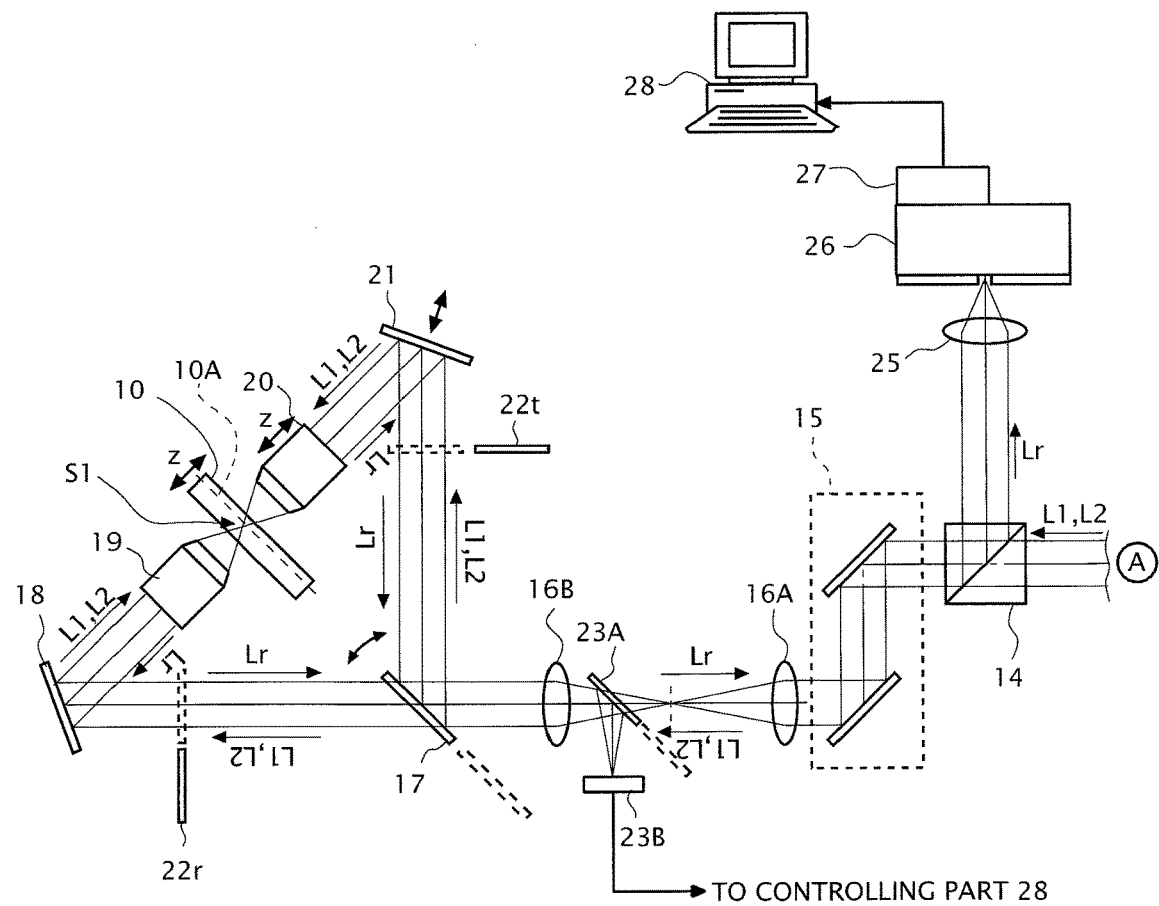

FIG. 1 is a configuration diagram of a CARS microscopy of the present embodiment. An upper part of FIG. 1 is a diagram illustrating a configuration of a light source side of the CARS microscopy, and a lower part of FIG. 1 is a diagram illustrating a configuration of a sample side of the CARS microscopy.

As illustrated in the upper part of FIG. 1, the CARS microscopy of the present embodiment includes a laser light source 11 and an excitation pulse light generating unit 12. Further, as illustrated in the lower part of FIG. 1, in the CARS microscopy of the present embodiment, a dichroic mirror 14, a light scanner 15, a relay optical system (lenses 16A, 16B), a movable beam splitter 17, a movable wavelength selection filter 22r, an all-reflective mirror 18, an objective lens 19, a transparent incubation container 10, an objective lens 20, a movable all-reflective mirror 21, a movable wavelength selection filter 22t, a beam splitter 23A, an imaging device 23B, a collecting lens 25, a spectroscope 26, a spectrum detector 27, and a controlling part 28 are further disposed.

Note that the incubation container 10 is a transparent container supported by a transmission-type sample stage (not illustrated), and in the inside of the incubation container 10, a transparent culture solution containing a living cell is accommodated. Molecules (protein, lipid and the like) contained in the living cell are observational objects of the CARS microscopy. Hereinafter, these molecules are referred to as "observational object molecules".

The laser light source 11 is a pulsed laser light source that oscillates a pulsed laser light, and a pulse shape of the pulsed laser light oscillated by the laser light source is set to an appropriate shape. By the setting, an energy density at a center portion of a spot S1 to be described later (high-density spot) becomes an energy density suitable for making the observation object molecule generate a CARS signal. The pulsed laser light emitted from the laser light source 11 is incident on the excitation pulse light generating unit 12.

The excitation pulse light generating unit 12 includes a lens 12A, a beam splitter 12B, a movable all-reflective mirror 12C, a movable all-reflective mirror 12D, a lens 12F, a photonic crystal fiber 12G, a lens 12H, a wavelength selection filter 12J, and a beam splitter 12E.

The pulsed laser light which is incident on the excitation pulse light generating unit 12 passes through the lens 12A to be turned into parallel pencil of light with a large diameter, and is then incident on the beam splitter 12B, in which the light is split into a pulsed laser light L1 that transmits through the beam splitter 12B and a pulsed laser light L1 that is reflected by the beam splitter 12B (note that in FIG. 1, the same reference numerals are given to two lights having mutually the same optical frequency).

First, the pulsed laser light L1 transmitted through the beam splitter 12B is incident on one end of the photonic crystal fiber 12G via the lens 12F. In the photonic crystal fiber 12G, a non-linear phenomenon such as self-phase modulation occurs in a propagation process of the pulsed laser light L1, and accordingly, the pulsed laser light L1 is converted into a coherent pulsed laser light with a large optical frequency band. Therefore, a white coherent pulsed light L2 is emitted from the other end of the photonic crystal fiber 12G. The white coherent pulsed light L2 passes through the lens 12H to be turned into parallel pencil of light with a large diameter, and is then incident on the beam splitter 12E via the wavelength selection filter 12J.

Meanwhile, the pulsed laser light L1 reflected by the beam splitter 12B is sequentially reflected by the all-reflective mirror 12C and the all-reflective mirror 12D to be incident on the beam splitter 12E, and is then combined coaxially with the white coherent pulsed light L2 on the beam splitter 12E.

Note that the whole part of the all-reflective mirrors 12C, 12D can be moved in directions of arrow marks in FIG. 1, and by the movement, a difference between an optical path length of the pulsed laser light L1 that is incident on the beam splitter 12E and an optical path length of the white coherent pulsed light L2 that is incident on the beam splitter 12E is adjusted. By the adjustment, a timing at which the pulsed laser light L1 is incident on the beam splitter 12E and a timing at which the white coherent pulsed light L2 is incident on the beam splitter 12E are matched.

Further, a characteristic of the wavelength selection filter 12J disposed on the optical path dedicated to the white coherent pulsed light L2 is set to a characteristic in which only an optical frequency component, out of a plurality of optical frequency components contained in the white coherent pulsed light L2, having an optical frequency lower than that of the pulsed laser light L1 is passed through the filter. Accordingly, the optical frequencies of all of the optical frequency components contained in the white coherent pulsed light L2 that is incident on the beam splitter 12E, are set to be lower than the optical frequency of the pulsed laser light L1 that is incident on the beam splitter 12E.

As described above, the pulsed laser light L1 and the white coherent pulsed light L2 having matched the optical paths and timings and having a difference in the optical frequencies are used as excitation light of the CARS microscopy. Hereinafter, such pulsed laser light L1 and white coherent pulsed light L2 are collectively referred to as "an excitation pulse light L1, L2".

Now, the excitation pulse light L1, L2 emitted from the beam splitter 12E in the upper part of FIG. 1 transmit through the dichroic mirror 14 illustrated in the lower part of FIG. 1, and are then incident on the lens 16A via the light scanner 15. The excitation pulse light L1, L2 which is incident on the lens 16A are collected by the lens 16A to be diverged again, and after passing through the beam splitter 23A, the light L1, L2 is incident on the lens 16B. The excitation pulse light L1, L2 is turned into parallel pencil of light by the lens 16B, and the resultant is then incident on the beam splitter 17. Note that a light-collecting plane (dotted line) of the excitation pulse light L1, L2 between the lens 16A and the lens 16B corresponds to a conjugate plane of a later-described observational object plane 10A.

Here, a part of the sample side from the beam splitter 17 is configured in a switchable manner, and by the switching, a mode of the CARS microscopy of the present embodiment is switched among the following five modes.

(a) Bilateral excitation & bilateral detection mode: a mode in which excitation pulse lights are irradiated to the incubation container 10 from both sides of the incubation container 10, and an interference intensity between white CARS signals emitted to the both sides of the incubation container 10 is detected.

(b) Bilateral excitation & unilateral detection mode: a mode in which excitation pulse lights are irradiated to the incubation container 10 from both sides of the incubation container 10, and a white CARS signal emitted to one side of the incubation container 10 is detected.

(c) Unilateral excitation & bilateral detection mode: a mode in which an excitation pulse light is irradiated to the incubation container 10 from one side of the incubation container 10, and an interference intensity between white CARS signals emitted to both sides of the incubation container 10 is detected.

(d) Transmitting observation mode: a mode in which an excitation pulse light is irradiated to the incubation container 10 from one side of the incubation container 10, and a white CARS signal emitted to the other side of the incubation container 10 is detected.

(e) Reflecting observation mode: a mode in which an excitation pulse light is irradiated to the incubation container 10 from one side of the incubation container 10, and a white CARS signal emitted to the same side of the incubation container 10 is detected.

(Bilateral Excitation & Bilateral Detection Mode)

First, the bilateral excitation & bilateral detection mode will be described.

In this mode, the wavelength selection filter 22*t* and the wavelength selection filter 22*r* are removed from optical paths, and the beam splitter 17 is inserted into the optical path, as illustrated in the lower part of FIG. 1.

Accordingly, the excitation pulse light L1, L2 which is incident on the beam splitter 17 is split into the excitation pulse light L1, L2 which is transmitted through the beam splitter 17, and the excitation pulse light L1, L2 which is reflected by the beam splitter 17.

First, the excitation pulse light L1, L2 transmitted through the beam splitter 17 is reflected by the all-reflective mirror 18 to be incident on the objective lens 19, and by being subjected to a light-collecting action of the objective lens 19, the excitation pulse light L1, L2 is collected toward a collecting point of the objective lens 19.

Meanwhile, the excitation pulse light reflected by the beam splitter 17 is reflected by the all-reflective mirror 21 to be incident on the objective lens 20, and by being subjected to a light-collecting action of the objective lens 20, the excitation pulse light is collected toward a collecting point of the objective lens 20.

Here, the objective lens 19 and the objective lens 20 have mutually the same focal length and mutually the same NA. Further, a focal plane of the objective lens 19 and a focal plane of the objective lens 20 are matched with the observational object plane 10A in a deep portion of the incubation container 10. Further, the collecting point of the objective lens 19 on the observational object plane 10A and the collecting point of the objective lens 20 on the observational object plane 10A are matched.

Therefore, the excitation pulse light L1, L2 directed from the objective lens 19 side toward the incubation container 10 and the excitation pulse light L1, L2 directed from the objective lens 20 side toward the incubation container 10 form the spot S1 at mutually the same position on the observational object plane 10A.

Furthermore, an optical path length of the excitation pulse light L1, L2 directed from the beam splitter 17 toward the observational object plane 10A via the all-reflective mirror 21 and the objective lens 20 and an optical path length of the excitation pulse light L1, L2 directed from the beam splitter 17 toward the observational object plane 10A via the all-reflective mirror 18 and the objective lens 19 are matched.

Specifically, in this mode, the optical path of the excitation pulse light L1, L2 directed toward the incubation container 10 is duplicated to a pair of optical paths, and a relationship between the pair of optical paths is set to a symmetric relationship with respect to the observational object plane 10A.

Accordingly, in this mode, one point (a portion at which the spot S1 is formed) on the observational object plane 10A is simultaneously irradiated by the excitation pulse light L1, L2 from both sides of the observational object plane 10A.

At a center portion of the spot S1 (high-density spot), a white CARS signal Lr is generated. The white CARS signal Lr includes a white CARS signal Lr emitted toward the objective lens 19 side, and a white CARS signal Lr emitted toward the objective lens 20 side.

The white CARS signal Lr directed from the high-density spot toward the objective lens 20 is passed through the objective lens 20, reflected by the all-reflective mirror 21, and is then incident on the beam splitter 17.

Meanwhile, the white CARS signal Lr directed from the high-density spot toward the objective lens 19 is passed through the objective lens 19, reflected by the all-reflective mirror 18 to be incident on the beam splitter 17, and is then combined coaxially with the white CARS signal Lr reached from the objective lens 20 side.

Here, in this mode, an optical path of the white CARS signal Lr emitted from the incubation container 10 is duplicated to a pair of optical paths, and the relationship between the pair of optical paths is set to the symmetric relationship with respect to the observational object plane 10A. Further, a pair of white CARS signals Lr that individually proceed through the pair of optical paths is coherent.

Therefore, in this mode, the pair of white CARS signals Lr emitted from the one point (the portion at which the spot S1 is formed) on the observational object plane 10A toward both sides are combined by the beam splitter 17, and the pair of white CARS signals Lr interfere with each other.

The pair of white CARS signals Lr (which are simply referred to as white CARS signal Lr, hereinafter) which is incident on the beam splitter 17 is incident on the dichroic mirror 14 via the lens 16B, the beam splitter 23A, the lens 16A, and the light scanner 15.

A characteristic of the dichroic mirror 14 is set to a characteristic in which the white CARS signal Lr is reflected by the mirror, and the excitation pulse light L1, L2 is transmitted through the mirror.

Accordingly, the white CARS signal Lr which is incident on the dichroic mirror 14 is reflected by the dichroic mirror 14.

Note that the light emitted from the spot S1 and capable of reaching the dichroic mirror 14 includes not only the white CARS signal Lr but also the excitation pulse light L1, L2 transmitted through or reflected by the incubation container 10. However, different from the white CARS signal Lr, the excitation pulse light L1, L2 transmits through the dichroic mirror 14.

Therefore, the white CARS signal Lr reflected by the dichroic mirror 14 is collected by the collecting lens 25 without being mixed with the excitation pulse light L1, L2, and the resultant is then incident on the spectroscope 26. Note that there is provided a pinhole at a collecting point of the white CARS signal Lr at a position in front of an incident port (slit) of the spectroscope 26.

The white CARS signal Lr which is incident on the inside of the spectroscope 26 is separated into a plurality of wavelength components (a plurality of optical frequency components) by a not-illustrated diffraction grating, and the wavelength components are individually incident on respective sensor parts of the spectrum detector 27 formed of line sensors and the like. Accordingly, the white CARS signal Lr which is incident on the inside of the spectroscope 26 is converted into a spectral signal by the spectroscope 26 and the spectrum detector 27. The spectral signal generated by the spectrum detector 27 is acquired by the controlling part 28.

Here, the light scanner 15 is a light scanner in which a pair of galvanometer mirrors and the like are disposed, and when the light scanner 15 is driven, the aforementioned spot S1 moves on the observational object plane 10A.

Therefore, the controlling part 28 drives the light scanner 15 to perform two-dimensional scanning on the observational object plane 10A with the spot S1, and acquires an output signal from the spectrum detector 27 when the spot S1 is at respective scanning positions, to thereby obtain spectra of the white CARS signal at respective positions on the observational object plane 10A, namely, a CARS spectral distribution. The CARS spectral distribution represents an oscillation mode distribution of the observational object (observational object position).

Here, a principle in which the white CARS signal is generated at the high-density spot, will be described in detail.

For the explanation, an optical frequency of the pulsed laser light L1 being one of the excitation pulse light L1, L2 is set to $\omega 1$, and optical frequencies of each optical frequency component $L2_1, L2_2, L2_3, L2_4, \ldots$ contained in the white coherent pulsed light L2 being the other of the excitation pulse light L1, L2 are set to $\omega 2_1, \omega 2_2, \omega 2_3, \omega 2_4, \ldots$.

At this time, a part having a natural frequency $\omega v_1$ that satisfies an expression of $\omega v_1 = \omega 1 - \omega 2_1$, out of the observational object molecule existed in the high-density spot, generates a CARS signal having an optical frequency of $\omega r_1 = 2\omega 1 - \omega 2_1$. Further, a part having a natural frequency $\omega v_2$ that satisfies an expression of $\omega v_2 = \omega 1 - \omega 2_2$, generates a CARS signal having an optical frequency of $\omega r_2 = 2\omega 2\omega_1 - \omega 2_2$. Further, a part having a natural frequency $\omega v_3$ that satisfies an expression of $\omega v_3 = \omega 1 - \omega 2_3$, generates a CARS signal having an optical frequency of $\omega r_3 = \omega 2\omega 1 - \omega 2_3$. Further, a part having a natural frequency $\omega v_4$ that satisfies an expression of $\omega v_4 = \omega 1 - \omega 2_4$, generates a CARS signal having an optical frequency of $\omega r_4 = 2\omega 1 - \omega 2_4$. Specifically, in the CARS microscopy of the present embodiment, the white coherent pulsed light L2 is used as one of the excitation pulse light L1, L2, so that the CARS signal generated at the high-density spot become a plurality of CARS signals with different optical frequencies, namely, the white CARS signal.

Here, attention is focused on one optical frequency component $L2_i$ contained in the white coherent pulsed light L2, and details of the CARS process caused by the optical frequency component $L2_i$ will be described.

Figure 2:
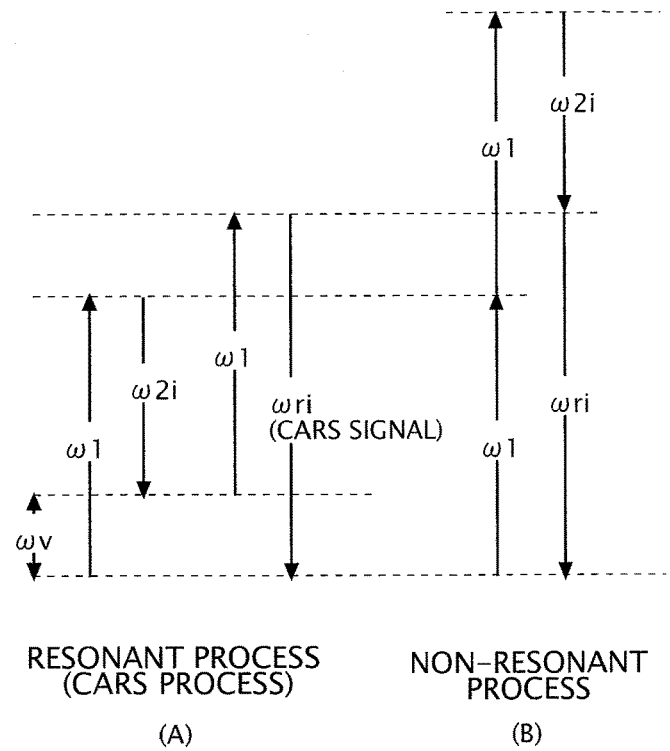
FIG. 2 is a diagram explaining a CARS process and a non-resonant process.

As illustrated in the left side of FIG. 2, the pulsed laser light L1 having the optical frequency $\omega 1$ and the optical frequency component $L2_i$ having an optical frequency $\omega 2_i$ generate a beat having an optical frequency of $(\omega 1 - \omega 2_i)$, and since a natural frequency $\omega v_i$ of a certain part of the observational object molecule is equal to the optical frequency $(\omega 1 - \omega 2_i)$ of the beat, that part is resonant with the beat, and a state of the part is changed to an excited state. Further, when the pulsed laser light L1 having the optical frequency $\omega 1$ is irradiated to the part in the excited state, the state of the part is changed to an intermediate state having an energy corresponding to $(\omega v_i + \omega 1)$. Thereafter, when the state of the part in the intermediate state is changed to a ground state, a CARS signal having an optical frequency of $\omega r_i = 2\omega 1 - \omega 2_i$ is generated.

Incidentally, according to this CARS process, an amplitude spread $\phi r$ (X, Y) of the CARS signal capable of being generated at the high-density spot (=an amplitude spread formed by the CARS signal on the observational object plane when a density of the observational object molecule is uniform) is represented by the following expression.

$$\phi r(X,Y) = \{\phi 1(X,Y)\}^2 \times \{\phi 2(X,Y)\}^*$$

Note that $\phi 1$ (X, Y) in this expression is a point image amplitude spread formed by the pulsed laser light L1 on the observational object plane, and $\phi 2$ (X, Y) in this expression is a point image amplitude spread formed by the optical frequency component $L2_i$ on the observational object plane.

Here, a background noise will be described.

At the high-density spot, not only the CARS process being one kind of resonant process but also a non-resonant process can take place. This non-resonant process is often caused by water molecules in the culture solution and cells, and is a process which becomes a main cause of the background noise. The non-resonant process caused by the water molecules takes place as will be described below. Specifically, as illustrated in the right side of FIG. 2, there is a possibility that the water molecule is subjected to two-photon excitation by the pulsed laser light L1 having the optical frequency $\omega 1$, and a state thereof is changed to an intermediate state having an energy corresponding to $2 \times \omega 1$. Thereafter, when the state of the water molecule in the intermediate state is changed to a ground state, a light induced by the optical frequency component $L2_i$ and having the same optical frequency $\phi 2_i$ as that of the optical frequency component $L2_i$, and a light having the same optical frequency $\omega 2_i$ as that of the CARS signal caused by the pulsed laser light L1 and the optical frequency component $L2_i$, are emitted. It is possible that these lights are emitted from the incubation container 10 and then reach the dichroic mirror 14.

Among these lights, the light having the optical frequency $\omega 2_i$ is not incident on the spectrum detector 27 since it is not reflected by the dichroic mirror 14, but, the light having the optical frequency $\omega r_i$ is reflected by the dichroic mirror 14 to be incident on the spectrum detector 27. Besides, the above-described phenomenon can occur in each of the plurality of optical frequency components $L2_i$ (i=1, 2, 3, . . . ) having different optical frequency $\omega 2_i$.

For this reason, it can be considered that a background noise with various optical frequencies is superposed on the CARS spectral distribution obtained by the controlling part 28.

Note that there is a characteristic that a phase is always shifted by $\pi/2$, between the background noise and the CARS signal, due to the difference between the non-resonant process and the CARS process.

Therefore, by performing an operation based on this characteristic on the aforementioned CARS spectral distribution, the controlling part 28 can remove the background noise with the various optical frequencies from the CARS spectral distribution. Therefore, the controlling part 28 can obtain a CARS spectral distribution including no background noise.

As described above, in the CARS microscopy of the present embodiment, both of the optical path of the excitation pulse light L1, L2 directed toward the incubation container 10 and the optical path of the white CARS signal Lr emitted from the incubation container 10 is duplicated to the pair of optical paths, and a relationship between the pair of optical paths is set to a symmetric relationship with respect to the observational object plane 10A.

Therefore, the mode of the CARS microscopy of the present embodiment can be set to the bilateral excitation & bilateral detection mode.

Note that in the CARS microscopy of the present embodiment, a posture of the beam splitter 17 is variable. By the adjustment of posture, an incident position of the excitation pulse light with respect to a pupil of the objective lens 20 and an incident position of the excitation pulse light with respect to a pupil of the objective lens 19 can be relatively adjusted. Therefore, by the adjustment, a position of the spot S1 formed by the objective lens 20 and a position of the spot S1 formed by the objective lens 19 can be relatively moved along the xy direction. Further, by the relative movement, a position in the xy direction of the spot S1 formed by the objective lens 20 and a position in the xy direction of the spot S1 formed by the objective lens 19 can be matched.

Further, in the CARS microscopy of the present embodiment, a position in the z direction of the objective lens 20 is variable, and by the positional adjustment, the focal plane of the objective lens 20 and the focal plane of the objective lens 19 can be matched.

Further, in the CARS microscopy of the present embodiment, the not-illustrated sample stage can adjust a position in the z direction of the incubation container 10, and by the positional adjustment, the focal planes of the objective lenses 19, 20 can be matched with a desired observational object plane 10A.

Further, in the CARS microscopy of the present embodiment, the all-reflective mirror 21 can be moved in a direction perpendicular to its reflection plane, while maintaining a posture thereof.

By the positional adjustment of the all-reflective mirror 21, a difference between the optical path length of the excitation pulse light L1, L2 directed from the objective lens 20 side toward the spot S1 and the optical path length of the excitation pulse light L1, L2 directed from the objective lens 19 side toward the spot S1 can be adjusted. By the adjustment, a timing at which the excitation pulse light L1, L2 is incident on the observational object plane 10A from one side and a timing at which the excitation pulse light L1, L2 is incident on the observational object plane 10A from the other side can be matched.

Further, by the positional adjustment of the all-reflective mirror 21, a difference between the optical path length of the white CARS signal Lr emitted from the spot S1 to the objective lens 20 side and the optical path length of the white CARS signal Lr emitted from the spot S1 to the objective lens 19 side can be adjusted. By the adjustment, a timing at which the white CARS signal Lr emitted to one side of the observational object plane 10A is incident on the beam splitter 17 and a timing at which the white CARS signal Lr emitted to the other side of the observational object plane 10A is incident on the beam splitter 17 can be matched.

Further, in the CARS microscopy of the present embodiment, the beam splitter 23A reflects a part of light directed from the lens 16B toward the conjugate plane (dotted line), and makes the part of light to be incident on the imaging device 23B which is disposed at a position equivalent to that of the conjugate plane. Therefore, if, at a time of the adjustment, a dummy sample (two-photon fluorescence element) is placed on the sample stage, and the controlling part 28 displays, in real time, a fluorescence image generated by the imaging device 23B on a monitor, a displacement in the z direction of the pair of spots S1 individually formed by the pair of objective lenses 19, 20, and a displacement in the xy direction of those pair of spots S1 can be visualized. Therefore, a user of the CARS microscopy can efficiently perform the positional adjustment of the objective lens 20 and the adjustment of posture of the beam splitter 17.

Note that in this case, the objective lens 20 is moved for matching the focal plane of the objective lens 20 and the focal plane of the objective lens 19, but, it is also possible to move the objective lens 19, instead of moving the objective lens 20.

Further, in this case, the all-reflective mirror 21 is moved for adjusting the difference between the optical path length of the excitation pulse light L1, L2 directed from the objective lens 20 side toward the observational object plane 10A and the optical path length of the excitation pulse light L1, L2 directed from the objective lens 19 side toward the observational object plane 10A, but, it is also possible to move the all-reflective mirror 18, instead of moving the all-reflective mirror 21.

Further, in this case, although it is set that the beam splitter 23A is not movable, the beam splitter 23A is required at the time of, not the observation, but the adjustment before observation, so that it is also possible that the beam splitter 23A is set to be movable, and is removed from the optical path when the observation is not performed. Further, if the beam splitter 23A is removed from the optical path when the observation is not performed, it is also possible to use an all-reflective mirror, instead of the beam splitter 23A.

Note that the CARS microscopy in the bilateral excitation & bilateral detection mode includes: a beam splitter (17) splitting an optical path of an illuminating light (L1, L2) supplied from a light source (11) into a pair of optical paths; a pair of deflecting mirrors (18, 21) individually deflecting the pair of optical paths toward mutually opposite sides of a specimen plane (10A) of a specimen (10); a pair of objective lenses (19, 20) individually disposed on the pair of optical paths and focusing on a common position on the specimen plane (10A); a dichroic mirror (14) disposed on a common part of the pair of optical paths, and separating a coherent object light occurred in a non-linear optical process at a collecting point (S1) of the pair of objective lenses (19, 20) from the illuminating light; a detecting unit (27) detecting the object light separated by the dichroic mirror (14) and generating a signal indicating light intensity at a light detecting part at which the object light is detected; and a controlling unit (28) repeatedly acquiring the signal generated by the detecting unit (27) while scanning the specimen plane (10A) by the collecting point (S1) and measuring a distribution of the signal on the specimen plane (10A).

(Bilateral Excitation & Unilateral Detection Mode)

Next, the bilateral excitation & unilateral detection mode will be described. Here, only a point of difference between this mode and the bilateral excitation & bilateral detection mode will be described.

Figure 3:
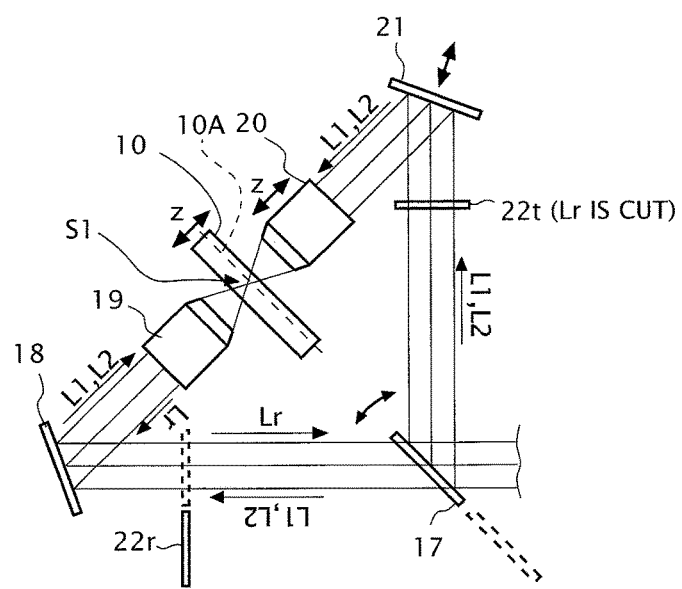
FIG. 3 is a diagram explaining a bilateral excitation & unilateral detection mode.

In this mode, the wavelength selection filter 22t is inserted into the optical path of the excitation pulse light L1, L2 directed from the beam splitter 17 toward the observational object plane 10A via the objective lens 20, as illustrated in FIG. 3.

A characteristic of the wavelength selection filter 22t is set to a characteristic in which the white CARS signal Lr is cut by the filter, and the excitation pulse light L1, L2 is transmitted through the filter.

Accordingly, in this mode, the excitation pulse light capable of reaching the observational object plane 10A is both the excitation pulse light L1, L2 emitted from the objective lens 19 and the excitation pulse light L1, L2 emitted from the objective lens 20, and the white CARS signal capable of reaching the beam splitter 17 is limited only to the white CARS signal Lr emitted from the observational object plane 10A to the objective lens 19 side (the white CARS signal Lr emitted to the objective lens 20 side cannot reach the beam splitter 17).

Note that the CARS microscopy in the bilateral excitation & unilateral detection mode corresponds to the CARS microscopy in the bilateral excitation & bilateral detection mode in which a wavelength selection filter (22t) disposed on one of the pair of optical paths, and cutting only the object light (Lr) among the illuminating light (L1, L2) directed toward the specimen plane (10A) and the object light (Lr) emitted from the specimen plane (10A) is further provided.

(Unilateral Excitation & Bilateral Detection Mode)

Next, the unilateral excitation & bilateral detection mode will be described. Also in this case, only a point of difference between this mode and the bilateral excitation & bilateral detection mode will be described.

Figure 4:
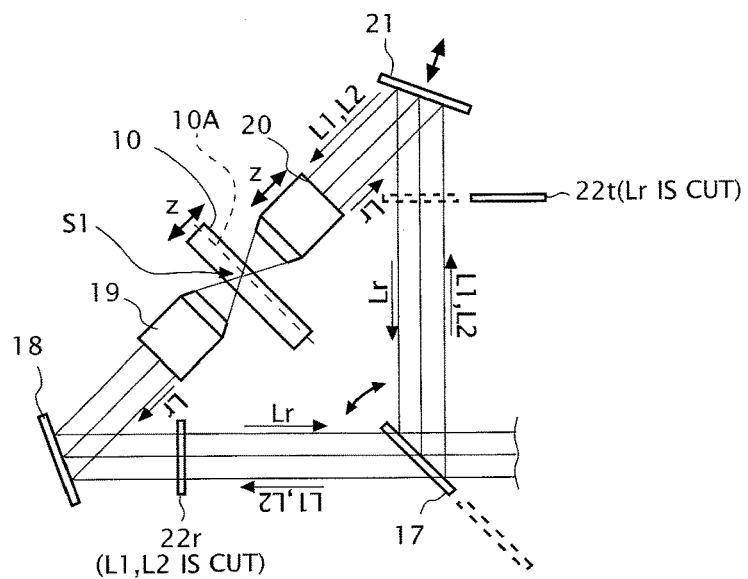
FIG. 4 is a diagram explaining a unilateral excitation & bilateral detection mode.

In this mode, the wavelength selection filter 22r is inserted into the optical path of the white CARS signal Lr directed from the observational object plane 10A toward the beam splitter 17 via the objective lens 19, as illustrated in FIG. 4.

A characteristic of the wavelength selection filter 22r is set to a characteristic in which the white CARS signal Lr is transmitted through the filter, and the excitation pulse light L1, L2 is cut by the filter.

Accordingly, in this mode, the excitation pulse light capable of reaching the observational object plane 10A is limited only to the excitation pulse light L1, L2 emitted from the objective lens 20, and the white CARS signal capable of reaching the beam splitter 17 includes both of the white CARS signal Lr emitted from the observational object plane 10A to the objective lens 20 side and the white CARS signal Lr emitted from the observational object plane 10A to the objective lens 19 side.

Note that the CARS microscopy in the unilateral excitation & bilateral detection mode corresponds to the CARS microscopy in the bilateral excitation & bilateral detection mode in which a wavelength selection filter (22r) disposed on one of the pair of optical paths, and cutting only the illuminating light (L1, L2) among the illuminating light (L1, L2) directed toward the specimen plane (10A) and the object light (Lr) emitted from the specimen plane (10A is further provided.

(Transmitting Observation Mode)

Next, the transmitting observation mode will be described. Also in this case, only a point of difference between this mode and the bilateral excitation & bilateral detection mode will be described.

Figure 5:
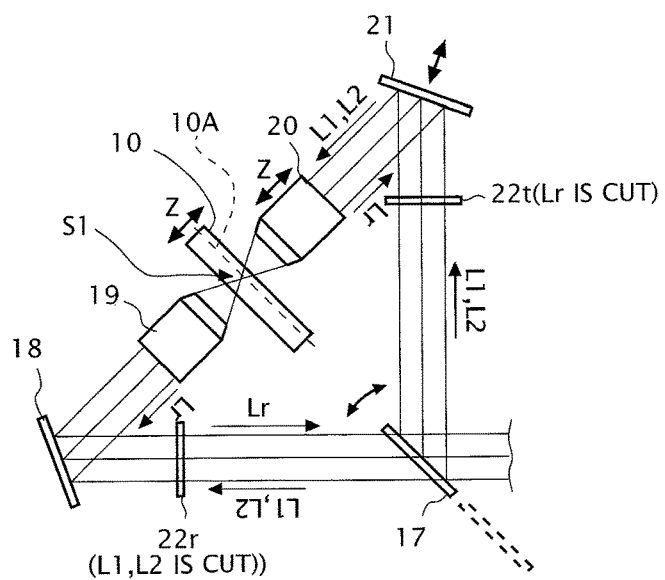
FIG. 5 is a diagram explaining a transmitting observation mode.

In this mode, the wavelength selection filter 22t is inserted into the optical path of the excitation pulse light L1, L2 directed from the beam splitter 17 toward the observational object plane 10A via the objective lens 20, and the wavelength selection filter 22r is inserted into the optical path of the white CARS signal Lr emitted from the observational object plane 10A to reach the beam splitter 17 via the objective lens 19, as illustrated in FIG. 5.

Accordingly, in this mode, the excitation pulse light capable of reaching the observational object plane 10A is limited only to the excitation pulse light L1, L2 emitted from the objective lens 20 side, and the white CARS signal capable of reaching the beam splitter 17 is limited only to the white CARS signal Lr emitted to the objective lens 19 side (namely, the white CARS signal Lr emitted to a downstream side of the excitation pulse light L1, L2).

(Reflecting Observation Mode)

Next, the reflecting observation mode will be described. Also in this case, only a point of difference between this mode and the bilateral excitation & bilateral detection mode will be described.

Figure 6:
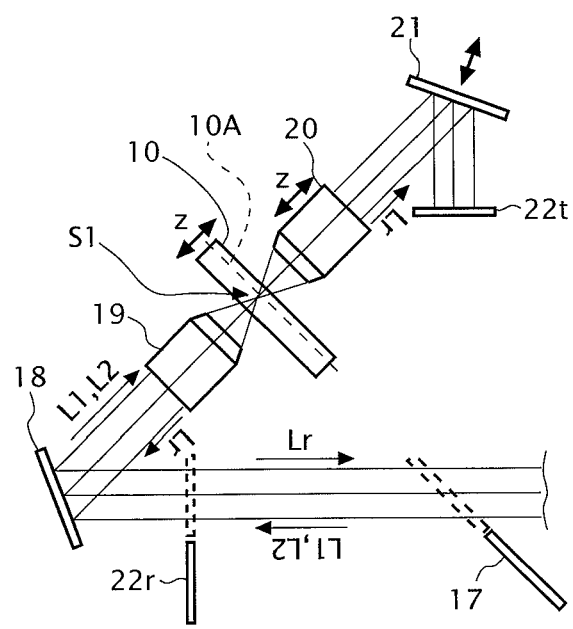
FIG. 6 is a diagram explaining a reflecting observation mode.

In this mode, the beam splitter 17 is removed from the optical path, and the wavelength selection filter 22t is inserted into the optical path of the white CARS signal Lr directed from the beam splitter 17 toward the observational object plane 10A via the objective lens 20, as illustrated in FIG. 6.

Accordingly, in this mode, the excitation pulse light capable of reaching the observational object plane 10A is limited only to the excitation pulse light L1, L2 emitted from the objective lens 19 side, and the white CARS signal capable of reaching the beam splitter 17 is limited only to the white CARS signal emitted to the objective lens 19 side (namely, the white CARS signal Lr emitted to an upstream side of the excitation pulse light L1, L2).

(Effects of Respective Modes)

Figure 7A:
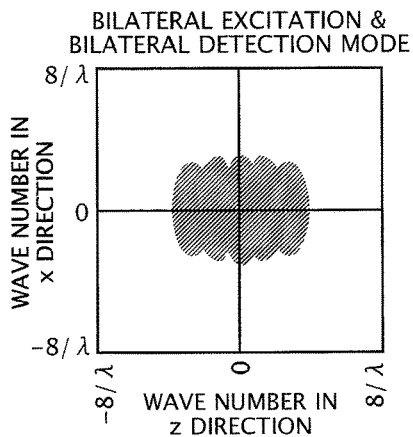
FIG. 7A to FIG. 7E are diagrams illustrating, for respective modes, spatial frequency ranges (transmission ranges) of structures capable of being transmitted from an observational object to a spectrum detector 27 side.
Figure 7B:
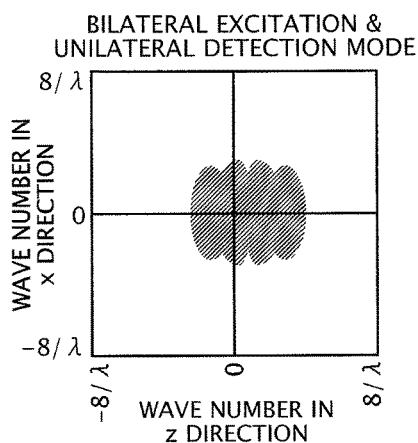
Figure 7C:
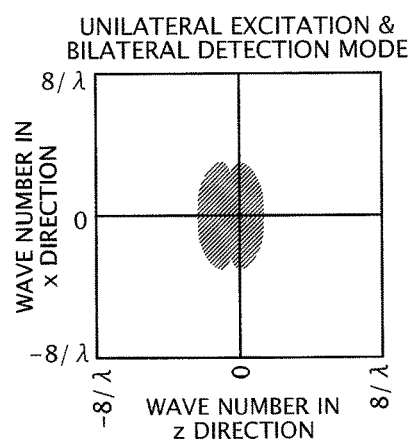
Figure 7D:
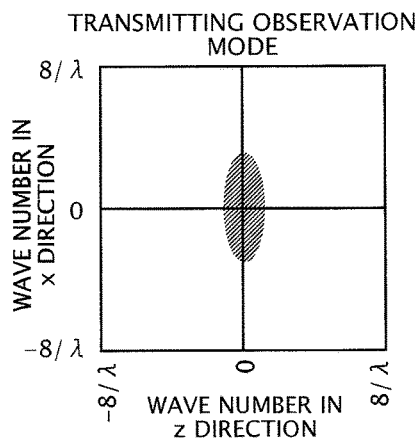
Figure 7E:
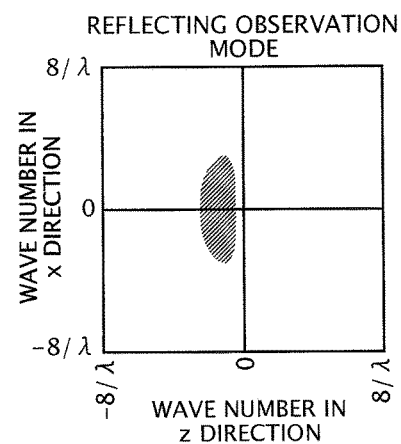

FIG. 7A to FIG. 7E are diagrams illustrating, for the respective modes, spatial frequency ranges (transmission ranges) of structures capable of being transmitted from the observational object to the spectrum detector 27 side. FIG. 7A illustrates the transmission range of the bilateral excitation & bilateral detection mode, FIG. 7B illustrates the transmission range of the bilateral excitation & unilateral detection mode, FIG. 7C illustrates the transmission range of the unilateral excitation & bilateral detection mode, FIG. 7D illustrates the transmission range of the transmitting observation mode, and FIG. 7E illustrates the transmission range of the reflecting observation mode.

Note that a horizontal axis and a vertical axis in each of these FIG. 7A to FIG. 7E indicate the transmission range in the z direction by a wave number, and the transmission range in the x direction by a wave number, respectively. Note that a range of the transmission range in the y direction is the same as a range of the transmission range in the x direction, so that an illustration thereof is omitted. Accordingly, it can be regarded that the wider the width in the z direction of the transmission range, the higher the observational resolution in the z direction, and the wider the width in the x direction of the transmission range, the higher the observational resolution in the xy direction.

As is apparent from the comparison of FIG. 7A to FIG. 7E, there is no difference, almost at all, in the observational resolution in the xy direction, among the modes. However, the observational resolution in the z direction is different among the modes.

Concretely, the highest observational resolution in the z direction is provided in the bilateral excitation & bilateral detection mode (FIG. 7A), the second-highest observational resolution in the z direction is provided in the bilateral excitation & unilateral detection mode (FIG. 7B), the third-highest observational resolution in the z direction is provided in the unilateral excitation & bilateral detection mode (FIG. 7C), and the fourth-highest observational resolution in the z direction is provided in the transmitting observation mode or the reflecting observation mode (FIG. 7D or FIG. 7E).

Specifically, in order to improve the observational resolution in the z direction, it is most desirable to set the mode of the CARS microscopy of the present embodiment to the bilateral excitation & bilateral detection mode (FIG. 7A), and also in a case where the mode is set to the bilateral excitation & unilateral detection mode (FIG. 7B), an effect which is close to the effect provided by the bilateral excitation & bilateral detection mode can be achieved. Further, also in a case where the mode is set to the unilateral excitation & bilateral detection mode (FIG. 7C), a certain effect can be achieved, although the effect is slightly inferior to that of the bilateral excitation & unilateral detection mode.

On the other hand, when the mode of the CARS microscopy of the present embodiment is set to the transmitting observation mode (FIG. 7D) and the reflecting observation mode (FIG. 7E), the observational resolution in the z direction is still low.

Incidentally, between the transmitting observation mode (FIG. 7D) and the reflecting observation mode (FIG. 7E), the transmission range is displaced, and there is a difference that the former mode covers an origin, but, the latter mode does not cover the origin. Specifically, there is a difference that, the transmitting observation mode (FIG. 7D) can transmit a structure in which the spatial frequency is in the vicinity of zero, although it cannot transmit a structure with large spatial frequency, and the reflecting observation mode (FIG. 7E) cannot transmit the structure in which the spatial frequency is in the vicinity of zero, although it can transmit the structure with large spatial frequency.

Therefore, a user of the CARS microscopy of the present embodiment can conduct the observation of the observational object plane 10A in detail, by repeatedly conducting the observation of the same observational object plane 10A while switching the mode of the CARS microscopy among the above-described five kinds of modes.

Further, by setting the mode of the CARS microscopy to the mode in which at least one of the direction of excitation and the direction of detection of the observational object plane 10A is duplicated to the pair of optical paths (FIG. 7A to FIG. 7C), it is possible to enhance the observational resolution in the z direction, and further, by setting the mode of the CARS microscopy to the mode in which both of the direction of excitation and the direction of detection of the observational object plane 10A are duplicated to the pair of optical paths (FIG. 7A), it is possible to maximize the observational resolution in the z direction.

Supplements to First Embodiment

Note that although the spectro-CARS microscopy is explained in the first embodiment, the present invention is also applicable to a non-spectro-CARS microscopy. In that case, it is only required to apply an optical parametric oscillator as the above-described excitation pulse light generating unit 12, and to generate a pair of pulsed laser lights having different optical frequencies as the excitation pulse light. Further, in that case, the CARS signal emitted from the observation object plane 10A become a CARS signal having a single optical frequency, so that a light detecting element such as a PMT (photo multiplier tube) may be used, instead of the spectroscope 26 and the spectrum detector 27.

Further, the laser scan-type CARS microscopy is explained in the first embodiment, but, the present invention is also applicable to a stage scan-type CARS microscopy. In that case, it is designed such that the light scanner 15 is omitted, and the not-illustrated sample stage can move the incubation container 10 not only in the z direction but also in the xy direction.

Further, the CARS process is utilized as the non-linear process in the first embodiment, but, it is also possible to utilize other non-linear processes. The other non-linear processes include, for example, a two-photon fluorescence, a first harmonic generation (SHG), a second harmonic generation (THG), a coherent Stokes Raman scattering (CSRS), a four-wave mixing (FWM), a sum frequency generation (SFG), and the like.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to the exact construction and operation illustrated and described, and accordingly all suitable modifications and equivalents may be resorted to, falling within the scope thereof.

What is claimed is:

1. A non-linear microscope, comprising:
an illuminating unit focusing an illuminating light supplied from a light source onto a specimen and generating thereby a coherent non-linear optical process at a collecting point at which the illuminating light is focused;
a detecting unit detecting a coherent object light which occurred in the non-linear optical process at the collecting point and generating a signal indicating light intensity at a light detecting part at which the object light is detected; and
a controlling unit repeatedly acquiring the signal generated by the detecting unit while scanning a specimen plane of the specimen by the collecting point and measuring a distribution of the signal on the specimen plane,
wherein at least one of an optical path of the illuminating light directed from the light source toward the specimen and an optical path of the object light directed from the specimen toward the light detecting part is duplicated to a pair of optical paths,
wherein a relationship between the pair of optical paths is set to a symmetric relationship with respect to the specimen plane, and
wherein the non-linear microscope further comprises:
a beam splitter being movable between a position at which the beam splitter is removed from the optical path of the illuminating light supplied from the light source and a position at which the beam splitter is inserted into the optical path of the illuminating light, and splitting the illuminating light into the pair of optical paths at the position at which the beam splitter is inserted into the optical path of the illuminating light;
a first wavelength selection filter moving between a state in which the first wavelength selection filter is removed from one optical path of the pair of optical paths and a state in which the first wavelength selection filter is inserted into the one optical path, and cutting the object light emitted from the specimen plane in the state in which the first wavelength selection filter is inserted into the one optical path; and a second wavelength selection filter moving between a state in which the second wavelength selection filter is removed from the other optical path of the pair of optical paths and a state in which the second wavelength selection filter is inserted into the other optical path, and cutting the illuminating light directed toward the specimen plane in the state in which the second wavelength selection filter is inserted into the other optical path, wherein a mode of the non-linear microscope is further configured to be switched between following five modes (a) to (e):

(a) bilateral irradiation and bilateral detection mode, which is a mode in which the beam splitter is held at the position at which the beam splitter is inserted into the optical path of the illuminating light and the first wavelength selection filter is held in the state in which the first wavelength selection filter is removed from the one optical path and the second wavelength selection filter is held in the state in which the second wavelength selection filter is removed from the other optical path, so that both of the optical path of the illuminating light and the optical path of the object light are duplicated, (b) bilateral irradiation and unilateral detection mode, which is a mode in which the beam splitter is held at the position at which the beam splitter is inserted into the optical path of the illuminating light and the first wavelength selection filter is held in the state in which the first wavelength selection filter is inserted into the one optical path and the second wavelength selection filter is held in the state in which the second wavelength selection filter is removed from the other optical path, so that the optical path of the object light is not duplicated, (c) unilateral irradiation and bilateral detection mode, which is a mode in which the beam splitter is held at the position at which the beam splitter is inserted into the optical path of the illuminating light and the first wavelength selection filter is held in the state in which the first wavelength selection filter is removed from the one optical path and the second wavelength selection filter is held in the state in which the second wavelength selection filter is inserted into the other optical path, so that the optical path of the illuminating light is not duplicated, (d) transmitting observation mode, which is a mode in which the beam splitter is held at the position at which the beam splitter is inserted into the optical path of the illuminating light and the first wavelength selection filter is held in the state in which the first wavelength selection filter is inserted into the one optical path and the second wavelength selection filter is held in the state in which the second wavelength selection filter is inserted into the other optical path, so that the optical path of the illuminating light and the optical path of the object light are not duplicated, and in which the object light emitted from the collecting point toward a downstream side of the illuminating light is detected, and (e) reflecting observation mode, which is a mode in which the beam splitter is held at the position at which the beam splitter is removed from the optical path of the illuminating light and the first wavelength selection filter is held in the state in which the first wavelength selection filter is inserted into the one optical path and the second wavelength selection filter is held in the state in which the second wavelength selection filter is removed from the other optical path, so that the optical path of the illuminating light and the optical path of the object light are not duplicated, and in which the object light emitted from the collecting point toward an upstream side of the illuminating light is detected.

2. The non-linear microscope according to claim 1, wherein
the illuminating unit splits the illuminating light supplied from the light source into a pair of illuminating lights and simultaneously irradiates the pair of illuminating lights toward a common position on the specimen plane from both sides of the specimen plane.

3. The non-linear microscope according to claim 1, wherein
the beam splitter combines, at a position in front of the light detecting part, a pair of object lights emitted from the collecting point to both sides of the specimen plane and makes the pair of the object lights interfere with each other.

4. The non-linear microscope according to claim 3, wherein
both of the optical path of the illuminating light and the optical path of the object light are duplicated.

5. The non-linear microscope according to claim 1, further comprising
a unit of adjusting a difference in an optical path length of the pair of optical paths.

6. The non-linear microscope according to claim 1, further comprising
a unit of adjusting a relative disposition relationship between the pair of optical paths with respect to the specimen plane.

7. The non-linear microscope according to claim 1, wherein
the controlling unit performs the scanning by moving the collecting point in a state where the specimen is kept fixed.

8. The non-linear microscope according to claim 1, wherein
the illuminating light includes a pair of laser lights having different optical frequencies.

9. The non-linear microscope according to claim 8, wherein:
one of the pair of laser lights further includes a plurality of laser lights having different optical frequencies; and
the detecting unit generates a signal indicating light intensity for each wavelength component.

10. The non-linear microscope according to claim 8, wherein
a combination of the optical frequencies of the pair of laser lights is set to a combination for making a molecule contained in the specimen cause a coherent anti-Stokes Raman scattering optical process.

11. A non-linear microscope, comprising:
a beam splitter being movable between a position at which the beam splitter is removed from an optical path of an illuminating light supplied from a light source and a position at which the beam splitter is inserted into the optical path of the illuminating light, and splitting the illuminating light into a pair of optical paths at the position at which the beam splitter is inserted into the optical path of the illuminating light;
a pair of deflecting mirrors individually deflecting the pair of optical paths toward mutually opposite sides of a specimen plane of a specimen;
a pair of objective lenses individually disposed on the pair of optical paths and focusing on a common position on the specimen plane;

a dichroic mirror disposed on a common part of the pair of optical paths and separating a coherent object light from the illuminating light, the coherent object light having been occurred in a non-linear optical process at a collecting point of the pair of objective lenses;

a detecting unit detecting the object light separated by the dichroic mirror and generating a signal indicating light intensity at a light detecting part at which the object light is detected;

a controlling unit repeatedly acquiring the signal generated by the detecting unit while scanning the specimen plane by the collecting point, and measuring a distribution of the signal on the specimen plane;

a first wavelength selection filter moving between a state in which the first wavelength selection filter is removed from one optical path of the pair of optical paths and a state in which the first wavelength selection filter is inserted into the one optical path, and cutting the object light emitted from the specimen plane in the state in which the first wavelength selection filter is inserted into the one optical path; and a second wavelength selection filter moving between a state in which the second wavelength selection filter is removed from the other optical path of the pair of optical paths and a state in which the second wavelength selection filter is inserted into the other optical path, and cutting the illuminating light directed toward the specimen plane in the state in which the second wavelength selection filter is inserted into the other optical path, wherein a mode of the non-linear microscope is further configured to be switched between following five modes (a) to (e):

(a) bilateral irradiation and bilateral detection mode, which is a mode in which the beam splitter is held at the position at which the beam splitter is inserted into the optical path of the illuminating light and the first wavelength selection filter is held in the state in which the first wavelength selection filter is removed from the one optical path and the second wavelength selection filter is held in the state in which the second wavelength selection filter is removed from the other optical path, so that both of the optical path of the illuminating light and the optical path of the object light are duplicated, (b) bilateral irradiation and unilateral detection mode, which is a mode in which the beam splitter is held at the position at which the beam splitter is inserted into the optical path of the illuminating light and the first wavelength selection filter is held in the state in which the first wavelength selection filter is inserted into the one optical path and the second wavelength selection filter is held in the state in which the second wavelength selection filter is removed from the other optical path, so that the optical path of the object light is not duplicated, (c) unilateral irradiation and bilateral detection mode, which is a mode in which the beam splitter is held at the position at which the beam splitter is inserted into the optical path of the illuminating light and the first wavelength selection filter is held in the state in which the first wavelength selection filter is removed from the one optical path and the second wavelength select ion filter is held in the state in which the second wavelength selection filter is inserted into the other optical path, so that the optical path of the illuminating light is not duplicated, (d) transmitting observation mode, which is a mode in which the beam splitter is held at the position at which the beam splitter is inserted into the optical path of the illuminating light and the first wavelength selection filter is held in the state in which the first wavelength selection filter is inserted into the one optical path and the second wavelength selection filter is held in the state in which the second wavelength selection filter is inserted into the other optical path, so that the optical path of the illuminating light and the optical path of the object light are not duplicated, and in which the object light emitted from the collecting point toward a downstream side of the illuminating light is detected, and (e) reflecting observation mode, which is a mode in which the beam splitter is held at the position at which the beam splitter is removed from the optical path of the illuminating light and the first wavelength selection filter is held in the state in which the first wavelength selection filter is inserted into the one optical path and the second wavelength selection filter is held in the state in which the second wavelength selection filter is removed from the other optical path, so that the optical path of the illuminating light and the optical path of the object light are not duplicated, and in which the object light emitted from the collecting point toward an upstream side of the illuminating light is detected.

12. The non-linear microscope according to claim 11, further comprising a wavelength selection filter disposed on one of the pair of optical paths and cutting only the object light among the illuminating light directed toward the specimen plane and the object light emitted from the specimen plane.

13. The non-linear microscope according to claim 11, further comprising a wavelength selection filter disposed on one of the pair of optical paths and cutting only the illuminating light among the illuminating light directed toward the specimen plane and the object light emitted from the specimen plane.

14. A non-linear observation method, comprising:

focusing an illuminating light supplied from a light source onto a specimen and making a coherent non-linear optical process take place at a collecting point at which the illuminating light is focused;

detecting a coherent object light occurred in the non-linear optical process at the collecting point and generating a signal indicating light intensity at a light detecting part at which the object light is detected; and repeatedly acquiring the signal generated in the detecting while scanning a specimen plane of the specimen by the collecting point, and measuring a distribution of the signal on the specimen plane, wherein at least one of an optical path of the illuminating light directed from the light source toward the specimen and an optical path of the object light directed from the specimen toward the light detecting part is duplicated to a pair of optical paths, and a relationship between the pair of optical paths is set to a symmetric relationship with respect to the specimen plane, and wherein the non-linear observation method further comprises:

moving a beam splitter, which splits the illuminating light into the pair of optical paths, between a position at which the beam splitter is removed from the optical path of the illuminating light supplied from the light source and a position at which the beam splitter is inserted into the optical path of the illuminating light;

switching a first wavelength selection filter, which cuts the object light emitted from the specimen plane, between a state in which the first wavelength selection filter is removed from one optical path of the pair of optical paths and a state in which the first wavelength selection filter is inserted into the one optical path; and switching a second wavelength selection filter, which cuts the illuminating light directed toward the specimen plane, between a state in which the second wavelength selection filter is removed from the other optical path of the pair of optical paths and a state in which the second wavelength selection filter is inserted into the other optical path, wherein the non-linear observation method further comprises switching between following five modes (a) to (e):

(a) bilateral irradiation and bilateral detection mode, which is a mode in which the beam splitter is held at the position at which the beam splitter is inserted into the optical path of the illuminating light and the first wavelength selection filter is held in the state in which the first wavelength selection filter is removed from the one optical path and the second wavelength selection filter is held in the state in which the second wavelength selection filter is removed from the other optical path, so that both of the optical path of the illuminating light and the optical path of the object light are duplicated, (b) bilateral irradiation and unilateral detection mode, which is a mode in which the beam splitter is held at the position at which the beam splitter is inserted into the optical path of the illuminating light and the first wavelength selection filter is held in the state in which the first wavelength selection filter is inserted into the one optical path and the second wavelength selection filter is held in the state in which the second wavelength selection filter is removed from the other optical path, so that the optical path of the object light is not duplicated, (c) unilateral irradiation and bilateral detection mode, which is a mode in which the beam splitter is held at the position at which the beam splitter is inserted into the optical path of the illuminating light and the first wavelength selection filter is held in the state in which the first wavelength selection filter is removed from the one optical path and the second wavelength selection filter is held in the state in which the second wavelength selection filter is inserted into the other optical path, so that the optical path of the illuminating light is not duplicated, (d) transmitting observation mode, which is a mode in which the beam splitter is held at the position at which the beam splitter is inserted into the optical path of the illuminating light and the first wavelength selection filter is held in the state in which the first wavelength selection filter is inserted into the one optical path and the second wavelength selection filter is held in the state in which the second wavelength selection filter is inserted into the other optical path, so that the optical path of the illuminating light and the optical path of the object light are not duplicated, and in which the object light emitted from the collecting point toward a downstream side of the illuminating light is detected, and (e) reflecting observation mode, which is a mode in which the beam splitter is held at the position at which the beam splitter is removed from the optical path of the illuminating light and the first wavelength selection filter is held in the state in which the first wavelength selection filter is inserted into the one optical path and the second wavelength selection filter is held in the state in which the second wavelength selection filter is removed from the other optical path, so that the optical path of the illuminating light and the optical path of the object light are not duplicated, and in which the object light emitted from the collecting point toward an upstream side of the illuminating light is detected.

* * * * *